US00PP27571P2

(12) United States Plant Patent
Hansen

(10) Patent No.: US PP27,571 P2
(45) Date of Patent: Jan. 17, 2017

(54) ***MONARDA* PLANT NAMED 'LILAC LOLLIPOP'**

(50) Latin Name: *Monarda didyma*
Varietal Denomination: Lilac Lollipop

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 10 days.

(21) Appl. No.: 14/545,861

(22) Filed: Jun. 30, 2015

(51) Int. Cl.
*A01H 5/02* (2006.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct plant cultivar of ornamental bee balm named *Monarda didyma* 'Lilac Lollipop' has rapid-growing, compact, branching stems, medium to dark green foliage, numerous lavender lilac flowers with reddish tinted stems. Foliage has good resistance to powdery mildew.

1 Drawing Sheet

BOTANICAL DESIGNATION AND CULTIVAR DENOMINATION

Botanical classification: *Monarda didyma.*
Variety denomination: 'Lilac Lollipop'.

CROSS REFERENCE TO RELATED PLANTS

FEDERAL SPONSORSHIP AND FUNDING

This plant invention was developed without federally sponsored research or development funding.

BACKGROUND OF THE INVENTION

The present invention relates to the new and distinct plant cultivar known as *Monarda didyma* 'Lilac Lollipop', and hereinafter also referred to solely as the cultivar 'Lilac Lollipop' or the "new plant". The new plant was the subject of an open pollination in summer of 2010 at a wholesale perennial nursery in Zeeland, Mich., USA. Seed was harvested by the inventor in the fall of 2010. The female or seed parent is the unreleased proprietary hybrid *Monarda dydima* H9-06-01 (not patented) and the male or pollen parent is unknown but may have been any one of several plants and seedlings in the isolation breeding area since the pollen is efficiently spread long distances by insects. The plant was initially subjected to evaluation in the summer of 2012 in trial plots of the same nursery in Zeeland, Mich. Final evaluation was performed in the summer of 2013 wherein a single selected seedling was separated for eventual introduction and assigned the breeder identification number H10-26-3.

*Monarda* 'Lilac Lollipop' has been asexually propagated by stem cuttings at the same nursery in the greenhouses in Zeeland, Mich., and the subsequent asexually propagated plants found to be stable and identical to the original selection.

BRIEF SUMMARY OF THE PLANT

*Monarda* 'Lilac Lollipop' is unique from its parent and all other bee balm plants known to the inventor. The nearest comparison varieties are 'Purple Rooster' (not patented), 'Leading Lady Lilac' U.S. Plant Pat. No. 26,431 and 'ACrade' (U.S. Plant Pat. No. 19,580) in plant habit. Compared to 'Purple Rooster', the new plant has larger flowers that are lighter colored, a lavender lilac rather than the darker purple, and 'Purple Rooster' is significantly taller. 'Lilac Lollipop' is slightly shorter than the female parent and taller than 'ACrade' and also has a more reddish coloring to the flowers than 'ACrade' or the female parent. Compared to both 'Leading Lady Lilac' U.S. Plant Pat. No. 26,431 and 'Leading Lady Plum' U.S. Plant Pat. No. 26,447, the new plant does not have the darker purple spotting on the petals and is much lighter with less red than 'Leading Lady Plum'.

The table below shows a more detailed comparison of these and other cultivars in terms of flower color and height.

TABLE 1

| CULTIVAR | FLOWER COLOR | HEIGHT |
|---|---|---|
| 'Achall' U.S. Plant Pat. No. 19,582 | deep red-purple | 45 cm |
| 'Acrade' U.S. Plant Pat. No. 19,580 | purple violet | 40 cm |
| 'Coral Reef' U.S. Plant Pat. No. 16,741 | coral pink | 125 cm |
| 'Fire Marshall' U.S. Plant Pat. No. 23,286 | deep red | 50 cm |
| 'Fireball' U.S. Plant Pat. No. 14,235 | red-purple | 60 cm |
| 'Lilac Lollipop' | lavender lilac | 46 cm |
| 'Leading Lady Lilac' U.S. Plant Pat. No. 26,431 | light lilac purple with dark spots | 32 cm |
| 'Leading Lady Plum' U.S. Plant Pat. No. 26,447 | magenta purple with dark spots | 34 cm |
| 'MCmum' U.S. Plant Pat. No. 22,136 | pink | 60 cm |
| 'Mondid 0803' U.S. Plant Pat. No. 17,513 | red-purple | 40 cm |
| 'Pardon My Pink' U.S. Plant Pat. No. 24,244 | fuchsia-pink | 28 cm |
| 'Pardon My Purple' U.S. Plant Pat. No. 22,170 | dark fuchsia | 30 cm |
| 'Petite Delight' U.S. Plant Pat. No. 10,784 | light pink-purple | 30 cm |
| 'Petite Wonder' U.S. Plant Pat. No. 13,149 | light pink | 25 cm |
| 'Pink Lace' U.S. Plant Pat. No. 18,367 | red-purple | 45 cm |
| 'Pink Supreme' U.S. Plant Pat. No. 14,204 | deep pink | 60 cm |
| 'Purple Rooster' | royal purple | 90 cm |
| 'Sugar Lace' U.S. Plant Pat. No. 22,918 | red-purple | 45 cm |

The following are traits of *Monarda didyma* 'Lilac Lollipop' that in combination distinguish it from all other bee balm known to the inventor:

1. Moderate growth rate, intermediate height, compact, tightly clumping habit.
2. Dark-green, powdery mildew resistant foliage.
3. Reddish tinted stems.
4. Lavender lilac flowers for a long period in summer.

BRIEF DESCRIPTION OF THE DRAWINGS

The photographs of the new plant demonstrate the unique traits of 'Lilac Lollipop' and the overall appearance of the plant at two-years-old at a nursery in Zeeland, Mich. The colors are as accurate as reasonably possible with current color reproduction technology. Deviation in ambient light spectrum, source and direction may cause the appearance of minor variation in color.

DETAILED BOTANICAL DESCRIPTION

Figure 1:
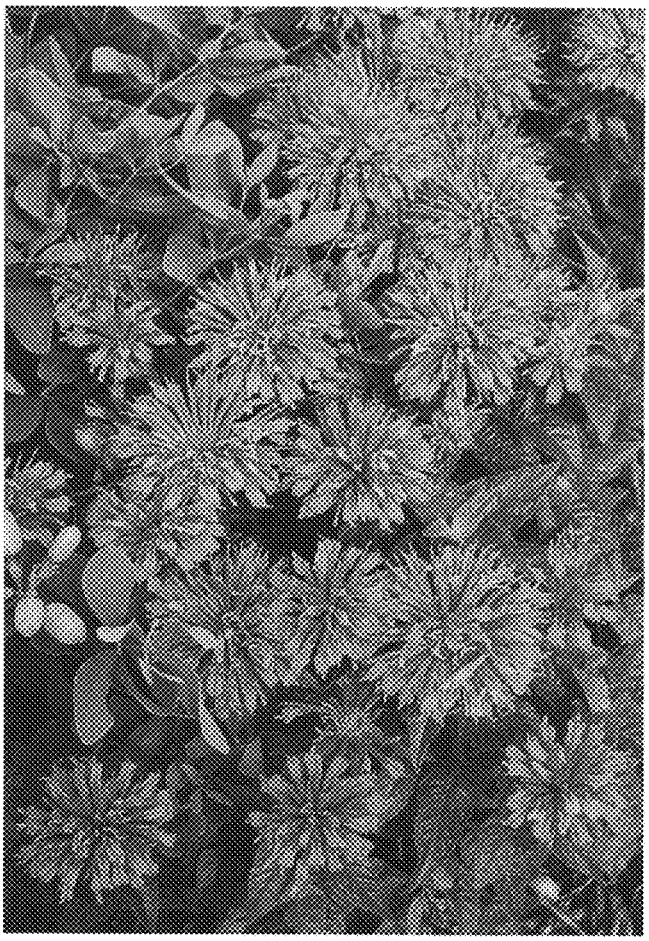
FIG. 1 shows the new plant in flower grow in full sun trial plot.
Figure 2:
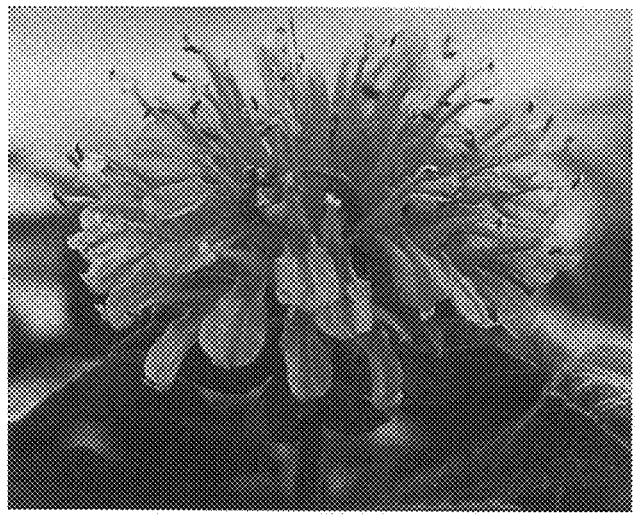
FIG. 2 shows a close-up of the flowers of a greenhouse grown plant.

The following descriptions and color references are based on the 2001 edition of The Royal Horticultural Society Colour Chart except where common dictionary terms are used. *Monarda didyma* 'Lilac Lollipop' has not been observed under all possible environments. The phenotype may vary slightly with different growing environments such as temperature, light, fertility, soil pH, moisture and maturity levels, but without any change in the genotype. The following observations and size descriptions are based on two-year old garden-grown plants in full sun at a nursery in Zeeland, Mich. with minimal supplemental fertilizer and water as needed but without plant growth regulators or pinching.

Botanical classification: *Monarda didyma.*

Parentage: Female (seed) parent is *Monarda didyma* H9-06-01 (not patented); male (pollen) parent is unknown.

Plant habit: Hardy, herbaceous, tightly compact perennial, producing several stems, spreading by short rhizomes; about 46.0 cm tall at flowering and about 57.0 cm wide; flowering begins mid-summer in Michigan and continues for about 5 to 7 weeks.

Propagation: Stem cuttings; Time to produce finished crop in 3.8 liter pots: about 7 to 9 weeks; moderately fast rate of growth.

Root: Fine, fibrous and freely branching; color creamy white to tan depending on soil type.

Leaves: Simple, lanceolate, opposite, serrated, slightly puberulent above and puberulent below; surfaces lustrous above, matte below; acute apex, ovate to rounded base; average about 6.0 cm long by about 3.1 cm wide.

*Leaf color.*—Young leaves between RHS 143B and RHS 141B above and between RHS 144B and RHS 138C below; older leaves between RHS 136B and RHS 136A above and between RHS 136B and RHS N138A below.

Foliage fragrance: Pleasantly lemony.

Veins: Pinnate, closed at margin; pubescent below with minutely puberulent above, slightly sunken above and raised below.

*Vein color.*—Adaxial midrib between RHS 138C and RHS 139D with tinting of between RHS N186D and lighter than RHS N77D toward the basal end and in areas of high light exposure, center portion of lateral veins nearest RHS 138C above with distal vein portion between RHS 136B and RHS 136A; abaxial midrib and center portion of lateral veins between RHS 138D and RHS 157B with distal portion of lateral veins between 136B and RHS N138A below.

Petiole: Pubescent, slightly concaved above; average about 3.0 mm long and 2.0 mm across.

*Petiole color.*—Adaxial between RHS 147D and RHS 139D with tinting of nearest RHS N77D where exposed to intense light, and abaxial nearest RHS 138C.

Stems: Squared, puberulent, densely pubescent at nodes; 3.0 to 6.0 mm across at base, average about 4.0 mm across; branched with four to six branches; about 50 stems per plant.

*Nodes.*—9 to 11 per stem; average internode length about 4.0 cm, widest in middle and closer at base; node color same as surrounding stem with some tinting of nearest RHS N186 D in regions of high light.

*Stem color.*—Between RHS 138C and RHS 139D with heavy tinting of between RHS N187A and RHS N186C, heaviest in regions or sides getting intense direct sunlight.

Flowers: Single labiate flowers arranged in terminal globular head to about 7.5 cm across and 4.5 cm tall opening from the center and progressing outwardly and down; individually persisting about 5 days in Michigan; numerous, about 250 flowers per head; self-cleaning.

*Flower fragrance.*—Moderately spicy.

Buds one to two days prior to opening: Narrowly oblanceolate, distinctly curved downward; about 2.2 cm long and 2.5 mm diameter.

*Bud color one to two days prior to opening.*—Nearest RHS 77B in the apical region with the center portion between RHS 77A and RHS 77B with a lighter base inside corolla of white, lighter than RHS N155D or RHS 155D.

Petals: Labiate; lower curved downward and upper nearly straight; split in two in the distal 1.1 cm with upper lip fused into a hood about 2.8 cm long and 2.5 mm diameter; lower lip about 3.0 cm long comprising three lobes including two side lobes about 1.0 mm long with rounded apex and center lobe about 4.0 to 5.0 mm long split in the distal 1.0 mm with acute apex, curled up almost 90 degrees; both side lobes glandular and pubescent outer surfaces with fine hairs the same color as petals; both lobes glabrous on inner surfaces.

*Petal color.*—Color of all petals on both surfaces upon opening between RHS 77A and RHS 77B with basal 5.0 mm white, lighter than RHS 155D or RHS N155D; two to three days after opening lower labellum ages to between RHS 77D and RHS 76B.

Filaments: Two, about 2.7 cm long by about 0.6 mm diameter across at the widest point.

*Filament color.*—Lighter than RHS N155D in the middle portion and below developing slight distal tinting of lighter than RHS 77D.

Anther: Oblong elliptic, dorsifixed, longitudinal; about 2.5 mm long by about 1.0 mm across.

*Anther color.*—Between RHS N187A and RHS N187B.

Pollen: Abundant, elliptic to globose, less than 0.1 mm; color nearest RHS 18C.

Pistil: One per flower.

Style: About 3.3 cm long by about 0.25 mm diameter; color lighter than RHS N155D with tinting increasing toward stigma to nearest RHS 70B.

Stigma: Split in two in the distal 2.0 mm, less than 0.25 mm in diameter; color nearest RHS 70B.

Ovary: Ovoid, 1.0 mm by 0.75 mm, lighter than RHS 145D.

Sepals: Five, entire, apiculate apex, base fused forming corolla about 9.0 mm long split in about the apical 2.0 mm, about 2.0 mm diameter at base and about 2.8 mm diameter at distal end; apex glandular and with minute hairs on outer surface, glabrous on inner surface.

*Sepal color*.—Nearest RHS 138B with longitudinal and marginal tinting of between RHS N186D and RHS N187B.

Peduncle: Pubescent, stiff, strong, branched, erect, squared to about 0.6 cm across at base and 37.0 cm long.

*Peduncle color*.—Between RHS 138C and RHS 139D with heavy tinting of between RHS N187A and RHS N186C, heaviest in regions or sides getting intense direct sunlight.

Bracts: Five to nine subtending flower head; acute apex with base sessile and truncate; size decreasing distally, to about 1.8 cm long and 1.5 cm wide at base.

*Bract color*.—Lowest bracts same color as leaves, distally becoming more marginally tinted nearest RHS 187A in both abaxial and adaxial surfaces; veining nearest RHS 138C on both surfaces.

Fruit: Single nutlet, elliptical, about 1.0 mm long and 0.7 mm wide; color nearest RHS 202A.

Hardiness: The new plant grows best with plenty of moisture and adequate drainage; hardy from at least from USDA zone 4 through 8.

Disease and pest resistance: Demonstrated powdery mildew resistance in side by side comparison at least equal that of 'ACrade' and better than 'AChall'.

I claim:

1. A new and distinct plant cultivar *Monarda didyma* 'Lilac Lollipop', as herein described and illustrated, resistant to powdery mildew and suitable for the garden landscape, or as a potted plant, patio, and for cut flower arrangements.

* * * * *